(12) United States Patent
Kaiser

(10) Patent No.: US 10,987,058 B2
(45) Date of Patent: *Apr. 27, 2021

(54) APPARATUS AND METHODS FOR OPTIMIZING VOLUME STATUS AND CARDIAC OUTPUT

(71) Applicant: CardioFlow Technologies, LLC, Nashville, TN (US)

(72) Inventor: Daniel Walter Kaiser, Palo Alto, CA (US)

(73) Assignee: CARDIOFLOW TECHNOLOGIES, LLC, Nashville, TN (US)

( * ) Notice: Subject to any disclaimer, the term of this patent is extended or adjusted under 35 U.S.C. 154(b) by 229 days.

This patent is subject to a terminal disclaimer.

(21) Appl. No.: 16/042,892

(22) Filed: Jul. 23, 2018

(65) Prior Publication Data

US 2019/0014993 A1 Jan. 17, 2019

Related U.S. Application Data

(63) Continuation of application No. 15/263,283, filed on Sep. 12, 2016, now Pat. No. 10,028,670, which is a (Continued)

(51) Int. Cl.
*A61B 5/00* (2006.01)
*A61N 1/365* (2006.01)
(Continued)

(52) U.S. Cl.
CPC ............ *A61B 5/6852* (2013.01); *A61N 1/365* (2013.01); *A61N 1/36514* (2013.01);
(Continued)

(58) Field of Classification Search
CPC . A61B 5/6852; A61B 5/02028; A61B 5/0205; A61B 5/02158; A61B 5/0261; A61B 5/029; A61B 5/0422; A61B 5/4848; A61N 1/365; A61N 1/36514; A61N 1/056; A61N 1/36564; A61N 1/36571; A61M 2025/0002; A61M 2025/0003
See application file for complete search history.

(56) References Cited

U.S. PATENT DOCUMENTS 10,028,670 B1 * 7/2018 Kaiser ................ A61N 1/36514
2017/0273587 A1 * 9/2017 Zhang ................ A61B 5/04011

* cited by examiner

*Primary Examiner* — Lindsey G Wehrheim
(74) *Attorney, Agent, or Firm* — William A. English; Vista IP Law Group LLP

(57) ABSTRACT

Systems and methods are provided for optimizing hemodynamics within a patient. Specifically, the system incorporates invasive sensor data (e.g., pressure measurements) combined with mechanisms to dynamically change the loading conditions of the heart and/or heart rate, in order to understand hemodynamic parameters. Computational analyses on dynamic sensor data are used to understand and guide heart rate, filling pressures, and/or volume resuscitation in critically ill patients. By pacing the heart or inducing tricuspid regurgitation, the system may cause dynamic changes in sensor data to understand optimal loading conditions and heart rates. While determining optimal hemodynamic parameters, the system may then automatically optimize the heart rate and/or filling pressures in critically ill patients.

19 Claims, 6 Drawing Sheets

Related U.S. Application Data continuation-in-part of application No. 14/597,190, filed on Jan. 14, 2015, now Pat. No. 9,878,080.

(60) Provisional application No. 62/927,038, filed on Jan. 14, 2014, provisional application No. 62/217,618, filed on Sep. 11, 2015.

(51) Int. Cl.

| | |
|---|---|
| *A61B 5/02* | (2006.01) |
| *A61B 5/029* | (2006.01) |
| *A61B 5/026* | (2006.01) |
| *A61B 5/0205* | (2006.01) |
| *A61B 5/042* | (2006.01) |
| *A61B 5/0215* | (2006.01) |
| *A61N 1/05* | (2006.01) |
| *A61M 25/00* | (2006.01) |

(52) U.S. Cl.
CPC ............ *A61B 5/0205* (2013.01); *A61B 5/029* (2013.01); *A61B 5/02028* (2013.01); *A61B 5/0261* (2013.01); *A61B 5/02158* (2013.01); *A61B 5/0422* (2013.01); *A61B 5/4848* (2013.01); *A61M 2025/0002* (2013.01); *A61M 2025/0003* (2013.01); *A61N 1/056* (2013.01); *A61N 1/36564* (2013.01); *A61N 1/36571* (2013.01)

APPARATUS AND METHODS FOR OPTIMIZING VOLUME STATUS AND CARDIAC OUTPUT

RELATED APPLICATION DATA

The present application is a continuation of co-pending application Ser. No. 15/263,283, filed Sep. 12, 2016, and issuing as U.S. Pat. No. 10,028,670, which claims benefit of provisional application Ser. No. 62/217,618, filed Sep. 11, 2015, and is a continuation-in-part of application Ser. No. 14/597,190, filed Jan. 14, 2015, now U.S. Pat. No. 9,878,080, which claims benefit of provisional application Ser. No. 62/927,038, filed Jan. 14, 2014, the entire disclosures of which are expressly incorporated by reference herein.

FIELD OF THE INVENTION

The present invention relates to apparatus, systems, and methods for monitoring and/or optimizing volume status in patients.

BACKGROUND

Volume status is a critical consideration when treating ill patients and arguably the most debated modifiable parameter. Patients who are felt to be hypovolemic, or "dry," are usually given volume resuscitation in hopes of improving cardiac output. Patients who are felt to be hypervolemic, or "wet," typically undergo diuresis, either from medication or dialysis machines. On average, fifty percent (50%) of all fluid boluses in Intensive Care Units do not improve cardiac output. In these patients, the additional volume does not benefit the patient. Rather, the extraneous volume may actually hurt the patient. Extraneous volume may reduce renal perfusion, inhibit wound healing, inhibit gut absorption, and/or compromise pulmonary function. In some cases, the additional fluid may actually worsen cardiac output, the precise parameter the fluid bolus was attempting to improve.

Thus, there is a need to improve the ability to determine volume status and subsequently volume responsiveness in patients.

There is growing data over the last decade suggesting the current 'gold standard' of volume status is suboptimal. The current management of determining volume status includes measurement of the central venous pressure (CVP) or pulmonary artery occlusion pressure (PAOP, or wedge pressure) as indicators of volume status. Newer 'dynamic' techniques, such as pulse pressure variation (the change in systemic blood pressure with respiration), have repeatedly outperformed the older, 'static' methods. However, the newer dynamic techniques have patient requirements that limit more widespread adoption of these methods. Pulse pressure variation is limited, amongst other limitations, to patients who are intubated, ventilated at high tidal volumes, and not spontaneously breathing. Furthermore, determining responses to these maneuvers are cumbersome and not easily accessible.

Described herein are various systems and methods aimed to measure and/or optimize volume status in ill patients.

Recently, there has been a growing emphasis on minimally invasive monitors of hemodynamic parameters. From external echocardiograms to complex interpretation of arterial waveforms, the industry has largely moved away from inserting long catheters into the body. However, this move is predicated on the lack of therapeutic benefit. As long as these monitors are purely diagnostic, it is understandable to minimize invasive procedures that place patients at risk. However, a temporary device that optimizes both heart rate and intra-cardiac filling pressures has the potential to improve cardiac output while optimizing pulmonary function. Such a device may benefit the patient and make an invasive procedure to insert the device both practical and beneficial.

The principle underlying CVP or PAOP-based fluid management presumes in a setting of low CVP or PCWP is that administering fluid boluses (and thereby increasing these parameters) will improve cardiac output, and this will have beneficial effects on tissue perfusion and lead to improved clinical outcome. Conversely, in the setting of an elevated CVP or PCWP, administering fluid boluses will fail to improve cardiac output; instead, the extraneous fluid may result in volume overload, leading to impaired wound healing, gut absorption, pulmonary congestion, and worsening renal function. The usefulness of the traditional CVP or PAOP-based recordings have been challenged by various studies indicating changes in right atrial pressure or PCWP in response to fluid challenge do not translate to favorable changes in cardiac output.

The second primary analysis of the FACTT trial, along with the ESCAPE and PACMAN trials in patients with acute decompensated heart failure and a mixed group of medical and surgical patients, have failed to show that fluid management guided by a pulmonary artery catheter (PAC) improves outcomes compared to use of central venous pressure. Disappointingly, these parameters, often employed by critical care physicians, appear to be no better (and perhaps worse) in predicting volume responsiveness than flipping a coin.

Many studies demonstrate the utility of 'dynamic measures' for volume status determination, the concept being that, for a given patient, the optimal filling pressures are variable, i.e., some patients require very high filling pressures to maintain cardiac output while other patients maximize their cardiac output at very low pressures. Therefore, the concept of 'dynamic' methods includes measuring changes in surrogates to cardiac output in response to perturbations to the system.

For example, spontaneous and mechanical ventilation are accompanied by dynamic changes in intrathoracic and transpleural pressures. These dynamic changes also result in changes in stroke volume as well as changes in blood pressure. A number of studies demonstrate that pulse pressure variation predicts fluid responsiveness in critically ill or perioperative patients. In a prospective study of forty patients with septic shock who were mechanically ventilated, pulse pressure variation (defined as 100%×(maximal pulse pressure−minimal pulse pressure)/(mean pulse pressure)) of greater than 15% predicted an increase in cardiac index with an area under the receiver-operating characteristic (ROC) curve of 0.98; the areas under the curve (AUC) for CVP and PCWP were 0.51 and 0.40. PPVar of greater than 15% predicted fluid responsiveness with 94% sensitivity and 96% specificity.

Another smaller prospective observational study employed a PPVar threshold of 12% and found this predicted fluid responsiveness with 68% sensitivity and 100% specificity; CVP and PCWP were not predictive of fluid responsiveness. In a study of off-pump coronary artery bypass graft patients, pulse pressure variation greater than 13% predicted an increase in cardiac index with a fluid challenge with an AUC of 0.81. CVP and PCWP were not significant predictors of change in cardiac index. In a small study of high-risk surgical patients, intra-operative fluid management based on pulse pressure variation decreased ICU length of stay by six days and reduced postoperative complications.

There are other respiratory maneuvers that can be used to predict volume responsiveness. A small study of mechanically ventilated patients reported that pulse pressure variation after a fifteen second end-expiratory occlusion predicted an increase in cardiac index with 91% sensitivity and 100% specificity. This measure was significantly more predictive of fluid responsiveness than passive leg raising (sensitivity 48%, specificity 91%). In another recent study of spontaneously breathing patients, pulse pressure changes in response to a Valsalva maneuver predicted fluid responsiveness with a sensitivity and specificity of 91% and 95% respectively. These studies highlight the important of dynamic maneuvers to predict volume-responsiveness.

Stroke volume/cardiac output and heart rate are complicated parameters. Although cardiac output is the product of heart rate with stroke volume (HR×SV=CO), numerous studies have found the cardiac output to be remain strikingly unaltered with changes in heart rate. This has been found in resting and exercising dogs and resting and exercising humans. In these studies, the lower stroke volume during atrial pacing was accompanied by a lower CVP, indicating a redistribution of blood from the venous beds to the arterial and peripheral vascular beds. As venous return to the heart is not increased, the stroke volume will decrease with increasing heart rate implying an extrathoracic venous collapse. Previous studies have found that increasing atrial pacing significantly decreased central venous pressure (CVP), pulmonary artery wedge pressure (PCWP), and pulse pressure. Furthermore, volume status measurements are also complicated by irregular heart rates such as atrial fibrillation or frequent ectopic beats. In particular, dynamic variables are difficult to interpret since filling pressures are frequently changing.

SUMMARY

The present invention relates to apparatus, systems, and methods for guiding and/or optimizing hemodynamics in patients, e.g. determining the benefit of volume resuscitation in hypotensive patients. More particularly, the present invention is directed to a temporarily placed device that may measure and/or induce mild perturbations to the intra-cardiac filling pressures and blood filling times in order to determine the optimal heart rate and volume status. The system may then advise on medical management, from volume resuscitation, diuresis, and medications affecting inotrope, afterload, and preload conditions. In addition, the device may improve cardiac output while preventing elevations in pulmonary pressures, thereby improving lung function and overall hemodynamics.

For example, systems and methods are provided for optimizing hemodynamics within a patient. Specifically, the system incorporates invasive sensor data (e.g., pressure measurements) combined with mechanisms to dynamically change the loading conditions of the heart and/or heart rate, in order to understand hemodynamic parameters. Computational analyses on dynamic sensor data are used to understand and guide heart rate, filling pressures, and/or volume resuscitation in critically ill patients. By pacing the heart or inducing tricuspid regurgitation, the system may cause dynamic changes in sensor data to understand optimal loading conditions and heart rates. While determining optimal hemodynamic parameters, the system may then automatically optimize the heart rate and/or filling pressures in critically ill patients.

Similar to traditional invasive monitoring devices, this device is likely to be inserted from a large peripheral vein, such as the right interval jugular vein, and advanced (typically with an inflatable balloon on the tip) into the right ventricular outflow tract or pulmonary artery. These invasive monitoring devices typically measure pulmonary pressure and/or pulmonary artery occlusion pressure (PAOP) in order to guide volume resuscitation. However, in order to determine (and deliver) the optimal heart rate and intra-cardiac filling pressures, the system needs to measure changes in hemodynamics in response to changes. By increasing the heart rate and/or inducing tricuspid regurgitation, the device can measure changes in pulmonary blood pressure and/or blood flow in order to understand (and then induce) the optimal heart rate and intra-cardiac filling pressures.

Standard catheters that measure pulmonary pressures, for example, the typical Swan-Ganz catheter, do not pace the heart or induce tricuspid regurgitation. While there are commercially available pulmonary arterial pressure monitors that also pace the heart, the pacing function is typically used due to abnormally low heart rates. The current system uses changes in heart rate in order to determine how filling times affect stroke volume and cardiac output. Therefore, the pacing function is both diagnostic and therapeutic. Likewise, at least one patent (U.S. Pat. No. 5,509,428) describes the concept of using a catheter to induce controllable tricuspid regurgitation. However, this system is designed to induce tricuspid regurgitation in order to treat congestive heart failure. The concept is not incorporated as a hemodynamic monitoring system that induces tricuspid regurgitation as a diagnostic maneuver to determine optimal volume status. Furthermore, without pacing the heart, cardiac output cannot be increased with this method.

The concept of using both pacing combined with inducing tricuspid regurgitation creates a new paradigm in the care of critically-ill patients. Perturbations in hemodynamic parameters (namely heart rate and intra-cardiac filling pressures) are adjusted with close monitoring of changes in blood pressure and/or blood flow in order to comprehensively understand the hemodynamic system. The device may then set the heart rate and controlled tricuspid regurgitation to the maximal parameters while also advising caretakers on optimal medical management. Pacing without regurgitation is suboptimal. Regurgitation without pacing is suboptimal. There is no available system or patent that describes a comprehensive invasive monitoring system that adjusts heart rate and/or controlled tricuspid regurgitation in order to determine and then optimize hemodynamic parameters. With more accurate blood flow measurements combined with pressure measurements, particularly with perturbations to these values, the system can estimate volume responsiveness that are superior to current methods.

In one embodiment, the device estimates left-sided filling pressures and cardiac output. Dynamic changes to hemodynamic parameters, induced by the pacing the heart or inducing regurgitation, are monitored by the device to estimate the likelihood of volume resuscitation benefiting the patient. Alternatively, the device may depend on natural or external perturbations to the hemodynamics in order to estimate volume responsiveness. For example, increasing the tidal volume during respiration may result in sufficient volume changes to affect stroke volume and/or filling pressures such that an estimate to volume responsiveness can be made. In other embodiments, the device may facilitate perturbations to the system by causing tricuspid regurgitation.

The device may be attached or respond to pressure measurements obtained in certain locations of the heart or body. One or more pressure sensors may be placed in the left atrium, pulmonary artery, the right ventricle, and/or the coronary sinus. From these pressure measurements, left-sided filling pressures may be estimated. In addition, the device may measure cardiac output. Cardiac output may be measured by thermodilution measurements, impedance measurements, and/or Doppler measurements. For example, miniaturized fiber-optic laser Doppler velocimetry sensors may be placed within the pulmonary artery to determine cardiac output through the right ventricle with very precise measurements. Doppler measurements may also use sound wave to measure blood flow. Additionally, pressure waveform analyses may be performed to estimate blood flow through the heart.

By measuring blood flow and/or intra-cardiac filling pressures, the pressure-stroke volume relationship of the left ventricle may be estimated (which is also called the Frank-Starling curve). Along with fluctuations in left ventricular stroke volume, the measurements may be combined to estimate how much volume resuscitation is expected to increase the cardiac output. The device may make estimations regarding the volume and capacitance of the pulmonary circulation, left atrium, and/or left ventricle. In one embodiment, the device paces the heart, for example the right atrium or right ventricle, and measures changes in blood flow and/or pressure over time to estimate the volume responsiveness of the left ventricle. Alternatively, the device may increase the heart rate to increase cardiac output to optimize hemodynamics. In some cases, the device may cause blood regurgitation to occur.

By reducing the stroke volume of the right ventricle, the device may improve the filling pressures of the left ventricle. Counterintuitively, inducing tricuspid regurgitation may paradoxically improve total cardiac output. Therefore, a computational system may make measurements regarding the heart rate, stroke volume, and intra-cardiac filling pressures; and adjust the heart rate and/or regurgitation volume to optimize hemodynamics. In addition, the computational system may make recommendations regarding volume resuscitation including the total amount of volume resuscitation recommended.

In one embodiment, the device includes a flow occlusion element. The device can therefore impede flow to the right ventricle in efforts to cause changes in left-sided filling pressures. These changes may be monitored by the device to determine the benefit of volume resuscitation. In other embodiments, the device includes the ability to sense and/or pace the atrium and/or ventricle of the heart. Therefore, the device may be able to use the diastolic interval in mathematical calculations. In addition, the device may pace the heart in order to evaluate volume status and/or improve cardiac output.

In another embodiment, blood flow is measured using two or more electrodes measuring impedance. As the blood pool around the electrode changes, so does the impedance. Calculations may be made utilizing the changes in impedance measurements in order to estimate blood flow with each contraction of the ventricle. Combining these measurements with pressure measurements may thus be combined to estimate volume responsiveness of the left ventricle.

The device may include pressure sensors along the catheter to help position the device. For example, the device may be advanced into the body while pressure recordings are monitored to determine the position of the device. For example, as soon as the pressure recordings transition from right atrial pressures to right ventricular pressures, the proceduralist may estimate the pressure sensor is within the vicinity of the tricuspid annulus. Once correctly positioned, the device may adjust pacing electrodes and/or other aspects of the device to affect blood flow. The atrial pacing system may include one or more electrodes that extend from the main body of the catheter, e.g., in response to a pulley mechanism, a plunger mechanism, or other actuator. A similar mechanism may be utilized to induce the controlled tricuspid regurgitation.

Cardiac output catheters have been previously described. However, these devices typically use thermodilution or similar methods to estimate cardiac output. Thermodilution measures temperature changes to fluid boluses to estimate cardiac output by monitoring temperature changes on a distal aspect of the catheter. This method estimates an average of cardiac output that occurs over numerous cardiac cycles. This method is inaccurate with tricuspid regurgitation and does not provide beat-to-beat estimations in cardiac output. In order to estimate pressure-stroke volume relationship of the left ventricle, more frequent and accurate measurements of blood flow are required. By measuring blood flow substantially continuously, and integrating over longer periods while measuring simultaneous changes in pressure, a true appreciation and calculation of volume responsiveness may be obtained. Furthermore, more precise measurements are required if cardiac output and/or flow changes are induced.

There have been tremendous advancements in pressure waveform analysis to estimate cardiac output. These computational analyses are leveraged in the current system such that small changes in blood pressure and/or blood flow are analyzed by the system to understand how heart rate and filling pressures affect blood flow and blood pressure. These calculations may then be used to direct the proceduralist (or performed automatically by the device) to accordingly adjust heart rate and/or tricuspid regurgitation to maximize hemodynamic parameters. The system controller may make recommendations regarding volume resuscitation or optimal heart rate. In other embodiments, the device may be programmed to adjust heart rate and/or blood flow as a diagnostic maneuver. Furthermore, the device may be programmed to automatically optimize both blood flow and/or heart rate within a pre-programmed window of parameters. For example, the device may determine that by increasing heart rate, the cardiac output may be increased with acceptable changes to intra-cardiac pressures. The device may then automatically increase the heart rate within the range of parameters entered into the device.

While increasing heart rate may increase cardiac output, equilibrium must be reached between the right and left ventricles. Frequently, one ventricle outperforms the other ventricle. If the right ventricle has a higher stroke volume than the left ventricle, increasing the heart rate may exacerbate the difference and increase pulmonary pressures. By increasing the heart rate while inducing tricuspid regurgitation, cardiac output may be maximized while preventing pulmonary pressures from increasing. Using this principle, the systems and methods herein may optimize both cardiac and pulmonary function.

Given the complex relationship between heart rate, filling pressures, and cardiac output, a computational system is required to interpret blood pressure waveform and/or flow rate to optimize hemodynamics. Detailed computational algorithms have not been included in current invasive monitoring systems.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Figure 1:
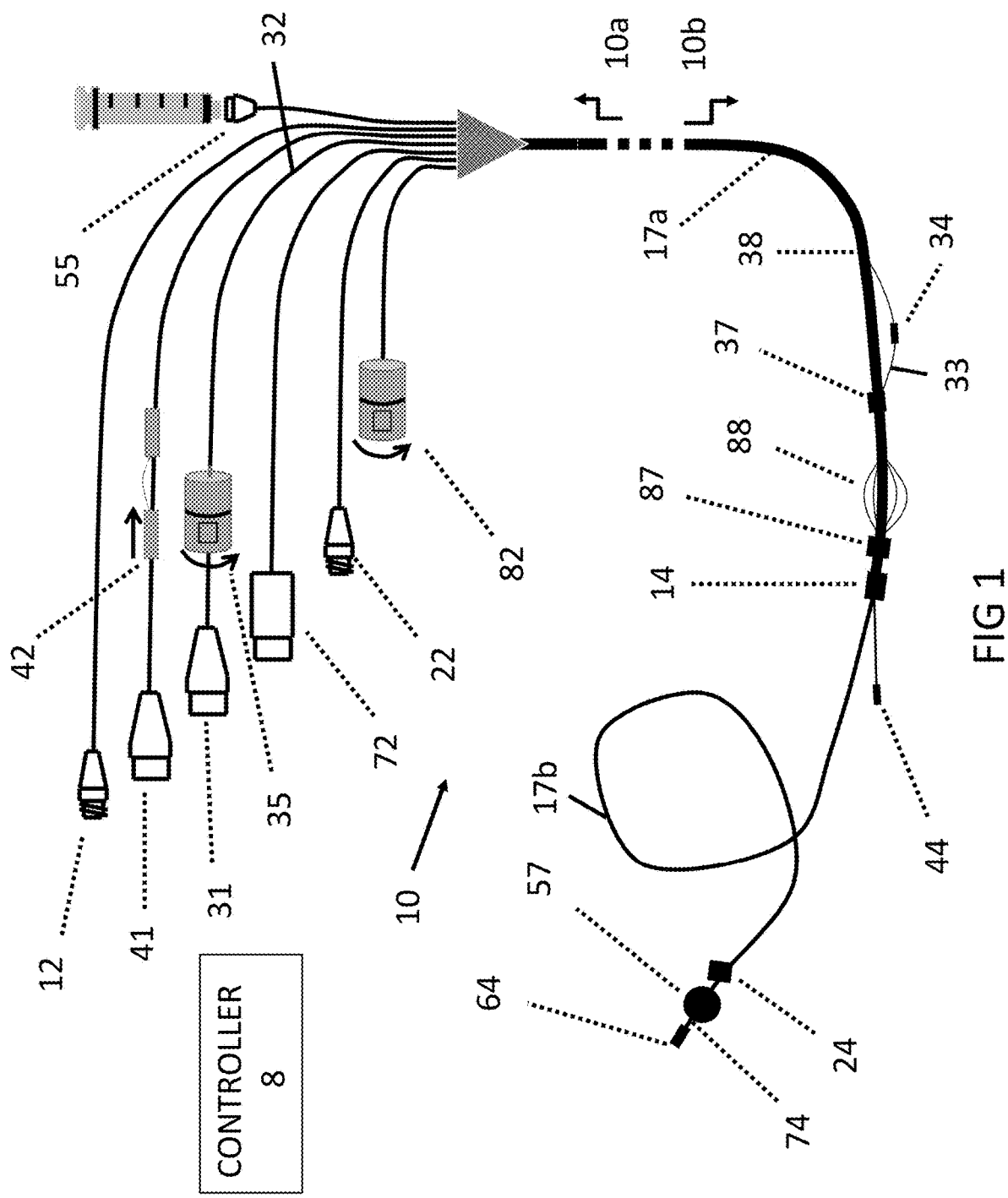
FIG. 1 is a schematic of an exemplary embodiment of a cardiac catheter.

Turning to the drawings, FIG. 1 shows an exemplary embodiment of a cardiac catheter 10 for introduction into a patient's body, e.g., to perform a diagnostic and/or therapeutic procedure within a patient's heart, as described elsewhere herein. As shown schematically in FIG. 1, the catheter 10 generally includes a handle or hub 10a including features that remain outside of the patient's body, e.g., including one or more connectors and/or actuators for the catheter 10, and an elongate tubular member 10b that is sized and/or otherwise configured for introduction into the patient's body carrying one or more elements for performing various functions.

The handle 10a of the catheter 10 may be coupled to a controller or processing unit 8 to provide a system for performing various functions, e.g., receiving data from one or more sensors carried by the tubular member 10b, performing various analyses, controlling one or more elements on the tubular member 10b, and/or displaying information, as described further elsewhere herein. Optionally, an intermediate portion may be provided between the handle 10a and tubular member 10b (represented by the dashed lines in FIG. 1 between 10a and 10b), which may be a tubular extension of the tubular member and/or other elongate member, which may remain partially outside the patient's body and/or may be at least partially introduced into the patient's body, e.g., to extend from an access site through the patient's vasculature such that the tubular member 10b is positioned within the patient's heart.

Figure 2:
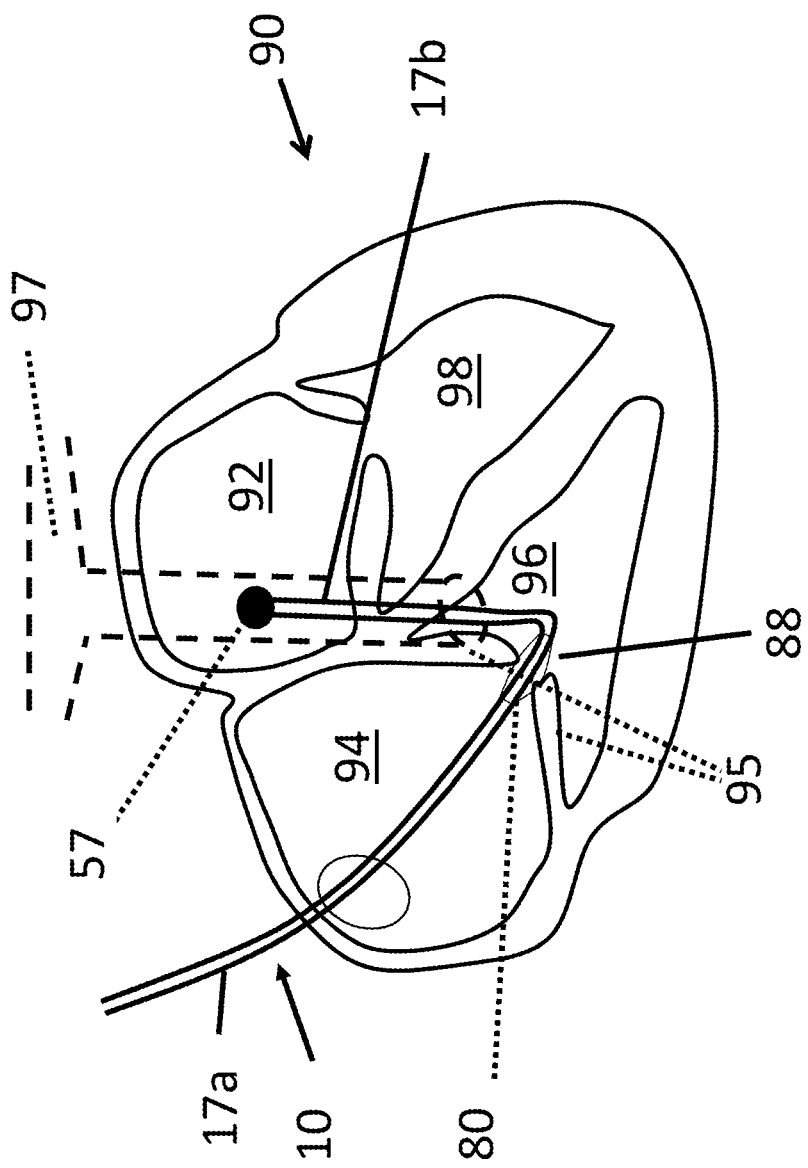
FIG. 2 is a cross-sectional view of a heart showing a distal portion of a catheter assembly, such as the catheter of FIG. 1, placed within the heart.

Generally, the tubular member 10b includes an elongated first or proximal segment 17a having a first cross-section and length designed to be inserted into the body of the patient, e.g., advanced through the patient's vasculature and into the patient's heart 90, and a second or distal segment 17b extending distally beyond the first segment 17a, e.g., having a second cross-section and length for extending into the pulmonary artery 97, e.g., as shown in FIG. 2. For example, the second segment 17b may have a smaller diameter or other cross-section than the first segment 17a, e.g., with a tapered or other transition (not shown) between the segments 17a, 17b, or the segments 17a, 17b may have a substantially uniform diameter or cross-section along their lengths. In addition, the first segment 17a may have a first length sufficient to place the elements thereon within one or more chambers of the patient's heart while the second segment 17b may have a relatively shorter second length to place the elements thereon within the patient's pulmonary artery, as described further elsewhere herein.

As shown in FIG. 1, the first segment 17a includes a plurality of elements spaced apart from one another along a distal portion of the first segment 17a, e.g., including one or more of an expandable proximal pacing structure 33, an expandable regurgitation structure 80, a first pressure port or sensor 14, and a distal pacing electrode 44. In addition, the second segment 17b includes one or more additional elements, e.g., one or more of a second pressure port or sensor 24, a balloon or other expandable device 57, a temperature sensor 74, and a flow measurement sensor 64. The elements may be mounted at desired positions along the length of the tubular member 10b to correspond to respective anatomical features or locations within a patient's heart 90, e.g., as shown in FIG. 2 and described further below.

For example, the pacing structure 33 may include an expandable strut carrying a first or atrial electrode 34, e.g., such that the electrode 34 may be extended away from the wall of the first segment 17a in order to position the electrode 34 in closer proximity to the right atrium 94 of the heart 90, e.g., to contact the myocardium of the right atrium 94 for the purposes of right atrial sensing and/or pacing. In one embodiment, the pacing strut includes a first fixed end 38 attached or otherwise fixedly coupled to the tubular member 10b and a second end coupled to a sliding mechanism 37, e.g., coupled to a first actuator 35 on the handle 10a via a wire or cable 32 (extending through a lumen within the tubular member 10b, e.g., as shown in FIG. 4).

Figure 4:
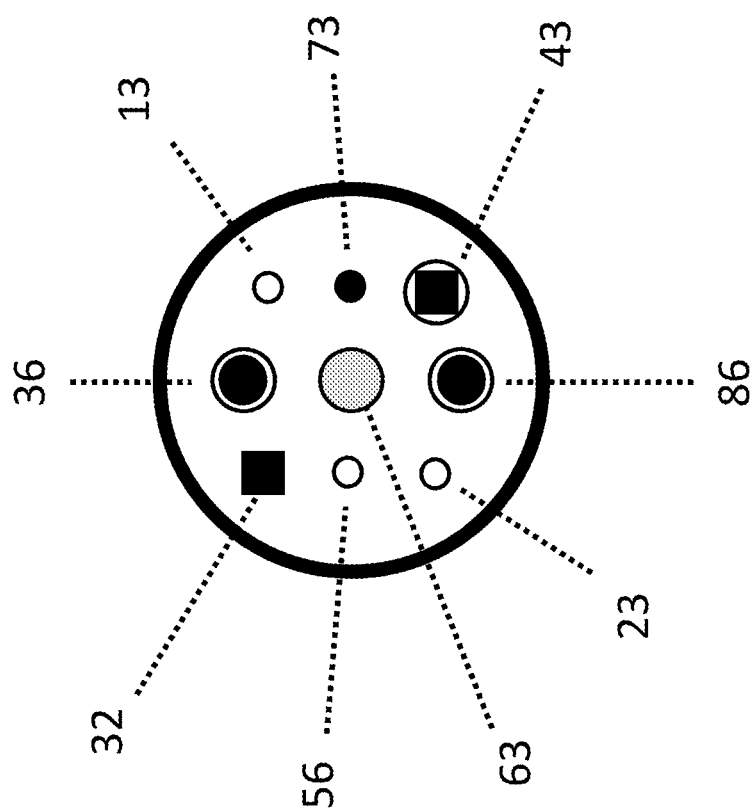
FIG. 4 is a cross-sectional view of an exemplary embodiment of a cardiac catheter body showing internal components of the catheter.

An atrial pacing connector 31 may be provided on the handle 10a, which may be coupled to the atrial electrode 34 by one or more wires (e.g., extending through a lumen within the tubular member 10b, as shown in FIG. 4). The atrial pacing connector 31 may be coupled to the controller 8 to sense electrical signals from and/or send electrical depolarizations to the atrial electrode 34 for delivery to the myocardium of the right atrium 94 (not shown). For example, the sliding mechanism 37 may include a sleeve or other structure movable axially along the first segment 17a between first and second positions using the first actuator 35. In an exemplary embodiment, the first actuator 35 may be rotatable as shown or slidable axially in a first direction relative to the handle 10a to cause the sliding mechanism 37 to move towards the first end 38, thereby causing the pacing structure 33 to bow outwardly and push the atrial electrode 34 away from the first segment 17a of the tubular member 10a and towards the myocardium for providing sensing and/or pacing when contacting the myocardium. It will be appreciated that the first actuator 35 may be moved to various positions to expand the pacing structure 33 any-where between a low profile delivery configuration (e.g., where the atrial electrode 34 is positioned against or immediately adjacent the wall of the first segment 17a, or, alternatively, into a recess in the wall) and a maximum expanded configuration.

Alternatively, the location of the fixed end 38 and the sliding mechanism may be reversed, i.e., with the first end 38 located distally, such that the first actuator 35 may be manipulated to advance the sliding mechanism 37 distally towards the fixed end 38, again pushing the atrial electrode 34 radially outwardly away from the first segment 17a towards the myocardium for sensing and/or pacing. Moving the first actuator 35 in a second direction opposite the first direction may retract the atrial electrode 34 radially inwardly, e.g., against the wall of the first segment 17a (or alternatively, into a recess in the wall) to provide a low profile configuration to facilitate introduction and/or other manipulation of the catheter 10. Alternatively, the pacing structure 33 may be biased to the low profile configuration such that, the first actuator 35 may be used to expand the pacing structure 33, yet when the first actuator 35 is released, the pacing structure 33 may automatically return to the low profile configuration.

The voltages sensed by the atrial electrode 34 may be displayed on a display monitor (not shown), e.g., included in or coupled to the controller 8, to facilitate the proceduralist in placing the catheter 10. For example, after using pressure recordings from the first pressure port 87 to correctly position the first segment 17a of the catheter 10, e.g., such that the atrial electrode 34 is disposed within the right atrium 94, the proceduralist may utilize the first actuator 35 to move the atrial electrode 34 away from the wall of the first segment 17a. The proceduralist may continue holding the first actuator 35 (or alternatively may lock the first actuator 35) to maintain the pacing structure 33 in the expanded configuration while monitoring the voltages obtained by the atrial electrode 34. It will be appreciated that the atrial electrode 34 may be a bipolar electrode or a unipolar electrode and/or that multiple electrodes (not shown) may be provided, as desired. If a unipolar electrode is utilized, a grounding electrode may be required externally on the patient's body or elsewhere on the catheter 10 (not shown). Once the sensed voltages are acceptable to the proceduralist, the pacing function of the atrial electrode 34 may be tested to make sure there is adequate capture of the atrial tissue.

In an alternative embodiment, the pacing structure 33 and/or the first segment 17a may include a plurality of electrodes (not shown) capable of atrial sensing and/or pacing. For example, the first actuator 35 may be connected to a plurality of splines or struts, each with one or more electrodes. The struts may be round wires, ribbons, and/or other structures capable of bowing outwardly or otherwise expanding as desired. In yet another alternative, one or more atrial electrodes may be carried on a balloon or other expandable device (not shown). Consequently, in this alternative, potential sensing and pacing electrodes may be enlarged in three-dimensional space, expanding radially outwardly away from the central first segment 17a in various directions.

Figure 3:
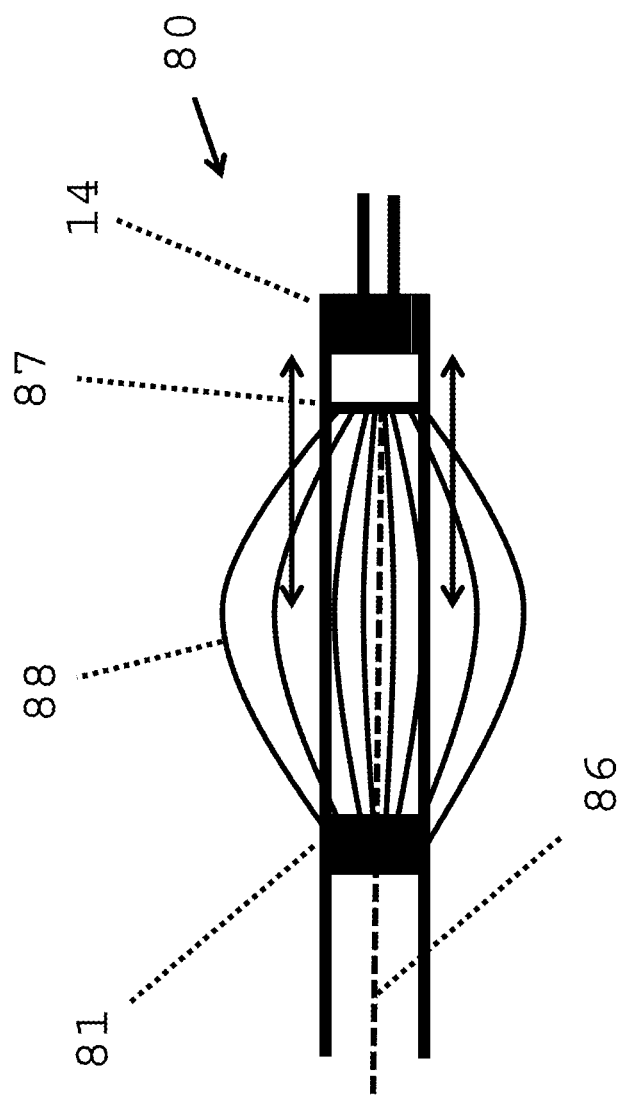
FIG. 3 is a side view of an exemplary embodiment of a regurgitating mechanism that may be included on a catheter assembly, such as the catheter of FIG. 1.

Turning to FIG. 3, a regurgitation structure 80 is shown that may be expandable generally similar to the expandable pacing structure 33, e.g., including a plurality of struts 88, to create controlled tricuspid regurgitation. For example, as shown in FIG. 3, the expandable regurgitation structure 80 may include a plurality of splines or struts 88 including first ends 81 attached to or otherwise fixed relative to the first segment 17a and second ends coupled to a sleeve or other slider 87. The slider 87 may be coupled to a second actuator 82 on the handle 10a via a second wire or cable 86 (also extending through a lumen within the tubular member 10b, as shown in FIG. 4) such that manipulation of the second actuator 82 may cause the struts 88 to selectively expand and collapse between a low profile and expanded profile. Alternatively, it will be appreciated that other expandable devices may be used for the regurgitation structure 80, e.g., a balloon, porous mesh, and the like (not shown), which may selectively open the tricuspid valve to allow blood flow therethrough. The first pressure port 14 is located between or adjacent the struts 88 of the regurgitation structure 80 and communicates with a first pressure connector 12 on the handle 10a (via a first pressure lumen 13 shown in FIG. 4) such the controller 8 may receive pressure information corresponding to the location of the regurgitation structure 80. The pressure information may be displayed or processed to facilitate positioning the regurgitation structure 80 within the patient's heart 90, e.g., within the tricuspid valve 95.

For example, as shown in FIG. 3, the first pressure port 14 may be located immediately distal to the regurgitation structure 80 such that pressure readings may be used to indicate when the first pressure port 14 enters the right ventricle 96 such that the regurgitation structure 80 may be positioned between the tricuspid valve 95. Once the regurgitation structure 80 is positioned within the tricuspid valve 95, the second actuator 82 may be manipulated (manually or automatically) to expand the struts 88, e.g., by pulling on the second cable 86 to direct the slider 87 towards the fixed ends 81. When this happens, the struts 88 are forced to bow radially outwardly away from the first segment 17a, thereby holding open aspects of the tricuspid valve 95, e.g., the leaflets and/or surrounding annulus, to induce tricuspid regurgitation. Thus, the proceduralist or the controller 8 may selectively actuate the regurgitation structure 80 to induce regurgitation through the tricuspid valve 95, as described elsewhere herein.

Returning to FIG. 1, optionally, the catheter 10 may also include a ventricular electrode 44 mounted on the first segment 17a distal to the regurgitation structure 80. Similar to the atrial electrode 34, a ventricular pacing connector 41 may be provided on the handle 10a, which may be coupled to the ventricular electrode 44 by one or more wires 42 (extending through a lumen within the tubular member 10b, e.g., as shown in FIG. 4). The ventricular pacing connector 41 may be coupled to the controller 8, which may sense and send electrical depolarizations to the ventricular electrode 44, e.g., when placed against myocardium of the right ventricle 96 (not shown).

Optionally, the ventricular electrode 44 may be carried on a wire or other element configured to be deployed from the first segment 17a, e.g., to contact myocardium of the right ventricle 96, as shown in FIG. 2. For example, a third actuator 42 may be coupled to the ventricular electrode 44 by a wire 43 designed to advance the ventricular electrode 44, e.g., once the first segment 17a of the catheter 10 is in a desired position and/or orientation. Alternatively, the ventricular electrode 44 may be mounted on an expandable structure, similar to the atrial electrode 34, may be mounted on a wall of the first segment 17a (not shown), or may be provided in other configurations, as desired.

Similar to the atrial electrode 34, the voltage waveform sensed by the controller 8 from the ventricular electrode 44 may be displayed to facilitate the proceduralist in safely advancing the ventricular electrode 44 for sensing and pacing of the right ventricle 96. In addition or alternatively, the controller 8 may selectively sense and pace via the ventricular electrode 44 (in addition to or instead of the atrial electrode 34) and, in combination with other parameters obtained from the catheter 10, may measure changes in the performance of the heart to provide information to the user and/or to automatically activate various elements of the catheter 10, e.g., expand the regurgitation structure 80 to induce regurgitation, modify heart rate, and the like, as described elsewhere herein.

Returning to FIG. 1, the construction of the catheter 10 may be substantially uniform or varied along the length of the first and second segments 17a, 17b, as desired. For example, the first segment 17a of the catheter 10 may be more firm and/or of a certain design up to the tricuspid regurgitation struts 88 than the second segment 17b, to facilitate placement of the first segment 17a at a desired position within the patient's heart. For example, in one embodiment, the catheter 10 is designed to be placed from the right interval jugular vein. The size and shape are designed such that the second segment 17b is substantially flexible to naturally travel to the right ventricular outflow tract while the first segment 17a of the catheter 10 may be less flexible to provide a framework in order to facilitate placement of the regurgitation structure 80, the atrial electrode 34, and ventricular electrode 44 within or adjacent the desired anatomical features. In addition, having a more firm structure may facilitate controlled regurgitation and/or pacing without reduced risk of blood flow or other action within the heart dislodging or otherwise undesirably moving the elements of the catheter 10. In some embodiments, the catheter 10 may include the regurgitation structure 80 without the electrodes 34, 44. In other embodiments, the catheter 10 may include only one or more pacing components, e.g., one or more both of the electrodes 34, 44 without the regurgitation structure 80.

With continued reference to FIG. 1, optionally, the second segment 17b may include a balloon or other expandable device 57. A balloon insufflator connector 55 may be provided on the handle 10a, which may be connected to a syringe or other source of inflation media (not shown) in order to inflate and deflate the balloon 57. The balloon 57 may be designed to float through the blood when inflated within the patient's heart 90, e.g., to position the balloon 57 in the pulmonary artery 97, as shown in FIG. 2. Optionally, the distal segment 17b may also have a distal pressure port or sensor 24, e.g., adjacent the balloon 57. A distal pressure connector 22 may be provided on the handle 10a, which may be connected to the controller 8 (or a separate pressure transducer, if desired) to measure the pressure of the blood near the distal pressure opening 24.

In one embodiment, pressure sensors 14, 24 may be mounted on the first and second segments 17a, 17b such that sensors 14, 24 may be exposed directly to regions adjacent the catheter 10 to provide signals corresponding to blood pressure. Alternatively, pressure sensors may be located on or within the handle 10a or within the controller 8 and tubing (not shown) may extend from the handle 10a or connectors 12, 22 to ports 14, 24 such that transduced pressure recordings are indicative of pressure recordings at the location of the ports 14, 24.

In one embodiment, a system, e.g., including the catheter 10 and controller 8 of FIG. 1, may be used to adjust blood flow within a patient's heart by causing ventricular dyssynchrony. In this embodiment, the catheter 10 may have one or more ventricular electrodes, e.g., electrode 44, which may be configured to come into contact with the right ventricular apex, right ventricular outflow tract, and/or the base of the right ventricle 96. The controller 8 may time pacing depolarizations with the cardiac cycle of the patient's heart in order to impair normal right ventricular function, thereby lowering pulmonary pressures and left-sided filling pressure.

Optionally, the catheter 10 and/or system may include one or more mechanisms to measure or approximate cardiac output. For example, as shown in FIG. 1, the catheter 10 may include a temperature sensor 74, e.g., mounted on the distal segment 17b, designed to measure temperature changes induced by injecting saline through the proximal pressure opening 14. In this embodiment, the handle 10a may include a temperature connector 72 coupled to the temperature sensor 74 via one or more wires 73 (e.g., extending through a lumen of the catheter, as shown in FIG. 4). The temperature connector 72 may be coupled to the controller 8 where the temperature information may be processed and displayed to treating caretakers.

Alternatively, the catheter 10 may also include various electrodes (not shown) whereby impedance changes during the cardiac cycle may be used to estimate cardiac output. In another alternative, the catheter 10 may include a Doppler sensor 64, e.g., a fiber optic cable 63 (e.g., extending through a lumen of the catheter 10, as shown in FIG. 4) and terminating at a distal end exposed on the distal segment 17b. A fiber optic connector 62 may be provided on the handle 10a that may be coupled to the controller 8 and used to estimate cardiac output by Doppler shifts measured at the distal end of the fiber optic cable 63. A distal tip of the fiberoptic cable 63 may include one or more lenses (not shown) or otherwise configured to optimize the ability to send and measure light for the determination of blood flow rates.

In addition or alternatively, the catheter 10 may also include one or more mechanisms to affect blood flow through the heart. For example, as described elsewhere herein, the first segment 17a of the catheter 10 may include a radially expandable regurgitation structure 80 configured to hold open the leaflets and/or annulus of the tricuspid valve 95 when expanded to induce tricuspid regurgitation in a controllable manner. For example, once the regurgitation structure 80 is positioned within the tricuspid valve 95, the second actuator 82 may be manipulated (manually by the proceduralist or automatically by the controller 8) to cause the struts 88 to change shape such that, once positioned along the tricuspid annulus, the regurgitation struts 88 hold the tricuspid valve 95 open.

Opening the tricuspid valve 95 may cause tricuspid regurgitation, thereby reducing forward flow. With the decrease in forward flow, cardiac output decreases, which may be measured using one or more of the sensors provided on the catheter 10, e.g., a blood flow and/or blood pressure sensor, such as those described above. In addition, the decrease in forward flow may decrease left-sided filling pressures, which may be estimated by analyzing waveforms measured from the distal pressure port 24. By affecting forward flow, the controller 8 may estimate the relationship between left-sided filling pressure and cardiac output; thereby assisting in the determination of fluid responsiveness.

In addition, the catheter 10 may be used to induce tricuspid regurgitation in the setting of volume and/or pressure overload to the left atrium 92 and/or the left ventricle 98 (not shown, see, e.g., FIG. 2). In addition, the controller 8 may use sensed data to optimize cardiac output by adjusting the patient's heart rate. In addition, by adjusting the heart rate, the catheter 10 may enable the determination of fluid responsiveness in methods similarly to those previously discussed.

For example, FIG. 2 is a schematic representation of a heart 90 after a catheter assembly, such as the catheter 10 of FIG. 1, has been placed within the heart 90. As described elsewhere herein, the first and second segments 17a, 17b of the catheter 10 may be introduced from an access site, e.g., a percutaneous site in a peripheral vessel, and advanced through the patient's vasculature into the patient's heart, e.g., into the right atrium 94 from the superior or inferior vena cava (not shown). In this figure, the catheter 10, specifically the balloon 57 and the second segment 17b, is guided through the right atrium 94, the right ventricle 96, and into the pulmonary artery 97. The regurgitation structure 80 is positioned within the tricuspid valve 95 such that by adjusting the struts 88, tricuspid regurgitation may be controlled, e.g., as described elsewhere herein to reduce forward flow of blood, e.g., to decrease cardiac output and/or otherwise modify performance of the heart 90. Once the patient has undergone desired monitoring and/or treatment, the catheter 10 may be withdrawn from the heart 90 and removed from the patient's body. In an alternative embodiment, the catheter 10 may be part of an implanted system, e.g., with the controller 8 also implanted such that the catheter 10 extends from the controller 8 into the heart 90 to provide indefinite monitoring and/or treatment, similar to the systems and methods described in U.S. Publication No. 2016/0199554.

Figure 5A:
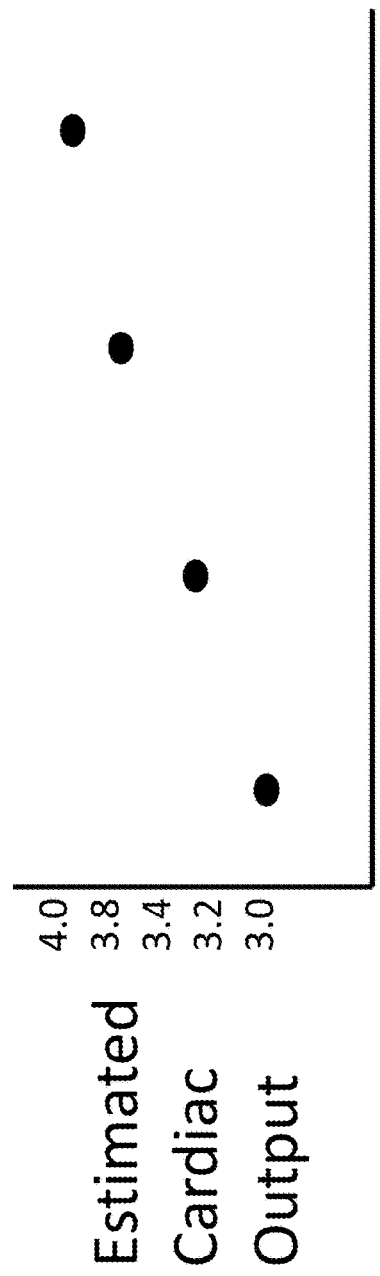
FIGS. 5A and 5B are graphs showing the relationship between cardiac output and left-sided intra-cardiac filling pressures depending on volume responsiveness.
Figure 5B:
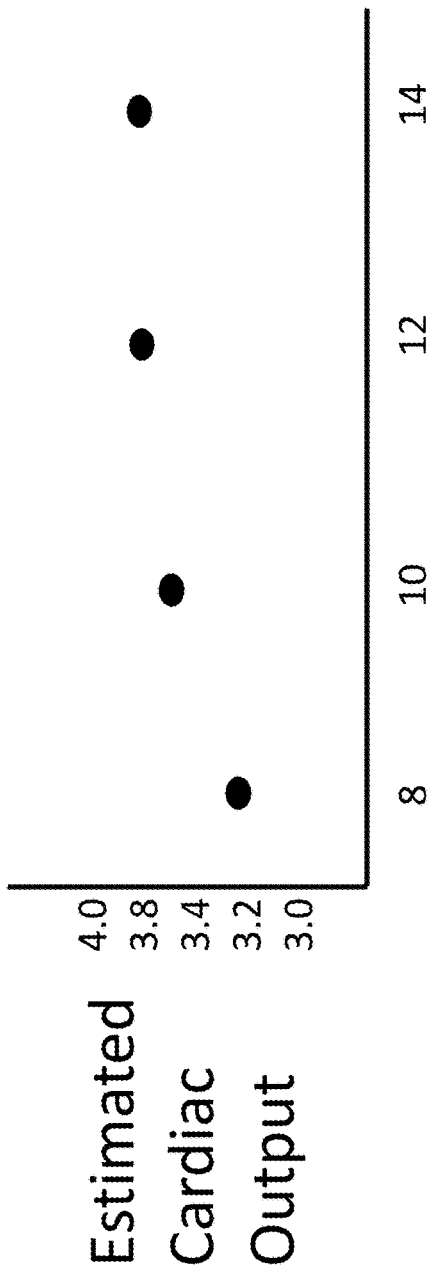

Turning to FIGS. 5A and 5B, tables are shown that demonstrate examples of the relationships between cardiac output and left-sided intra-cardiac filling pressures depending on volume responsiveness. In FIG. 5A, reductions in estimated left ventricular end diastolic pressure (LVEDP) may result in reductions in estimated cardiac output. This relationship suggests the patient may benefit from volume resuscitation, if the caretakers believe that cardiac output should be increased. FIG. 5B demonstrates one example of a patient less likely to respond to volume resuscitation. In this figure, reductions in LVEDP do not significantly reduce the estimated cardiac output. This situation suggests the patient may benefit from diuresis or persistent induced tricuspid regurgitation. Depending on further analysis between heart rate and/or filling parameters, the data may suggest the patient may benefit from increased heart rate. In addition, in some circumstances, the patient may benefit from both increase in heart rate and induced tricuspid regurgitation.

Figure 6:
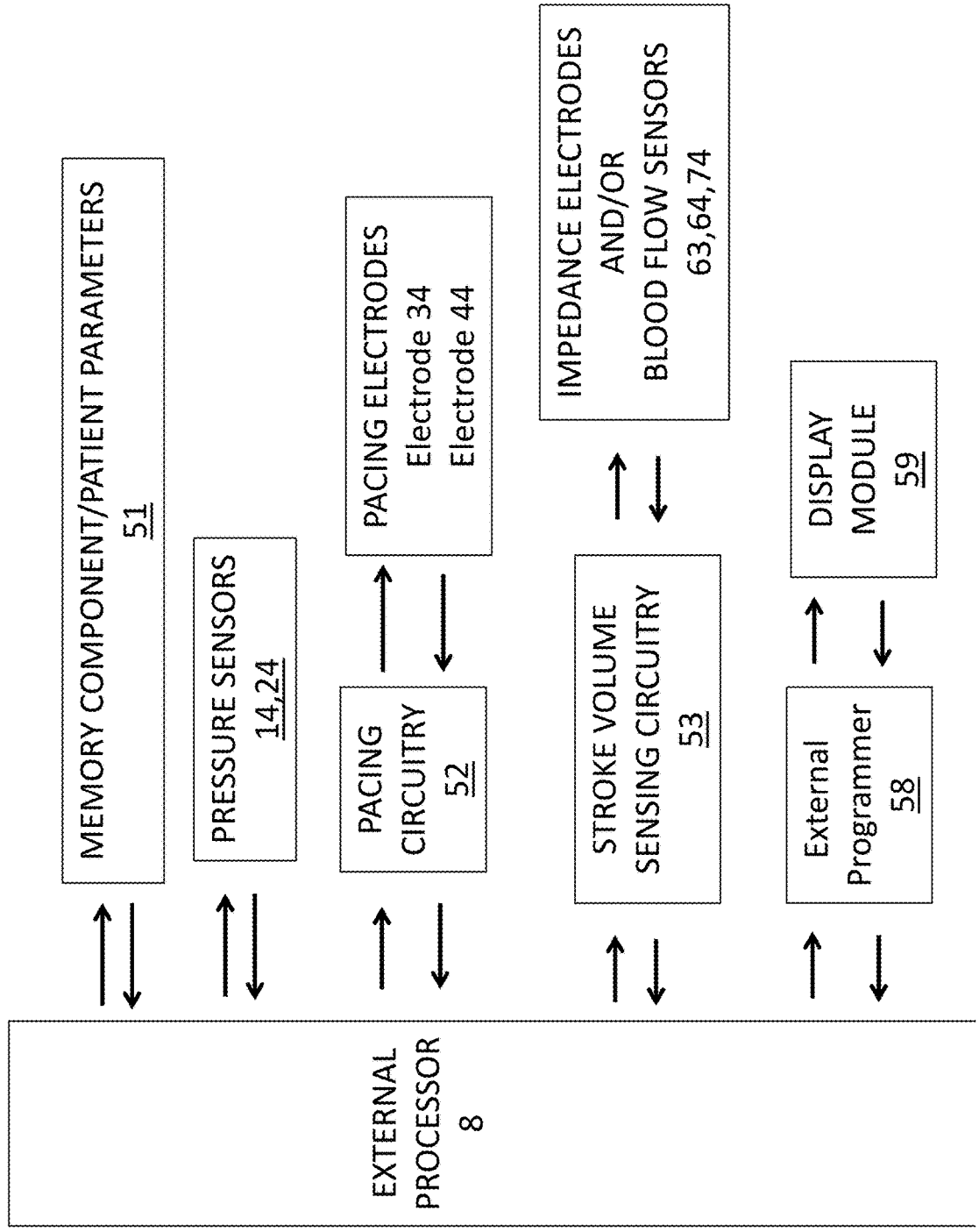
FIG. 6 is a functional block diagram of an exemplary embodiment of circuitry for a controller or processing unit for a catheter, such as the catheter of FIG. 1.

Turning to FIG. 6, a simplified functional block diagram is shown of an exemplary embodiment of the components located within and/or connected to an external processor or controller 8. As described above, the controller 8 may be coupled to elements of a catheter, such as catheter 10 of FIG. 1, via one or more connectors on the handle 10a. Although separate connectors are shown in FIG. 1, it will be appreciated that a single connector or multiple connectors may be provided between the handle 10a and the controller 8 in order to receive data from the elements and/or control elements on the catheter 10. For example, similar elements may have their connectors, e.g., electrodes 34, 44 and their connectors 31, 41 or pressure ports 14, 24 and their connectors 12, 22, contained in a single connector housing such that they are simultaneously connected to the controller 8.

Once the connectors of the handle 10a are coupled to the controller 8, the controller 8 may receive sensor information from various components, e.g., one or more of electrodes 34, 44, pressure ports 14, 24, temperature sensor 74, and Doppler sensor 64, in order to provide analyses regarding the overall hemodynamics of the patient in order to predict volume responsiveness and optimal heart rate. In addition, the controller 8 may selectively (e.g., automatically or when activated by the user) activate elements of the catheter 10 within the patient's heart 90, e.g., the electrodes 34, 44 for pacing, the balloon 57, and/or the regurgitation structure 80. In addition or alternatively, the elements of the catheter 10 may be manually activated by the user directly, as desired.

For example, as shown, the controller 8 is connected to memory component/patient parameters 51, pressure sensors 14 and 24, pacing circuitry 52, stroke volume sensing circuitry 53, and an external programmer 58. The patient parameters 51 may include patient parameters (such as patient weight or laboratory values or medication the patient is receiving). The pacing circuitry 52 is electrically coupled to the electrodes, for example, electrodes 34 and 44, thereby allowing the controller 8 to sense electrical activity (such as myocardial depolarizations), deliver pacing stimulations, and/or deliver defibrillation or cardioversion shocks, as desired. The stroke volume sensing circuitry 53 may be connected to impedance electrodes (such as electrode 34 and 44 and, optionally, to additional other electrodes not shown). These electrodes may sense change in impedance values at periods of the cardiac cycle to estimate stroke volume.

In another embodiment, the stroke volume sensing circuitry 53 may be connected to blood flow sensors (e.g., 63, 64, and 74). This circuitry may include light Doppler technology to measure blood flow. In one embodiment, the controller 8 may also be connected to a sensor or indicator regarding the degree of tricuspid regurgitation (also not shown). The controller 8 may be connected to an external programmer 58 that may connect to a display module 59 in order to facilitate communication between the control processor 51 and other components of the system external to the patient. Therefore, in one exemplary embodiment, the controller 8 may combine pressure waveform data obtained from the pressure sensors (14, 24), blood flow data from flow sensors (63, 64, 74), heart rate sensors from pacing electrodes (34, 44), and regurgitation indicator (not shown), combined with patient parameters 51 in order to determine volume responsiveness and/or optimal heart rates. In one embodiment, the controller 8 may automatically adjust heart rate and/or the amount of tricuspid regurgitation in order to maximize hemodynamic parameters.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for monitoring and/or treating a patient, comprising:
    an elongate member comprising a distal portion designed to be inserted into a patient's heart and advanced into a pulmonary artery of the heart;
    at least one sensor on the distal portion for measuring blood pressure;
    an electrode structure on the distal portion carrying one or more electrodes; the electrode structure configured to extend the one or more electrodes outwardly away from the distal portion to contact myocardial tissue for the purposes of sensing and pacing the heart;

a processor that performs computational analyses on sensed parameters in order to estimate volume responsiveness and/or optimal heart rates; and a regurgitation structure on the distal portion comprising a radially expandable portion configured to hold open leaflets of a tricuspid valve of the heart to induce tricuspid regurgitation in a controllable manner.

2. The system of claim 1, further comprising one or more sensors for measuring sensor data corresponding to blood flow through one of a right ventricle or pulmonary artery of the heart.

3. The system of claim 2, wherein the one or more sensors are configured to provide sensor data corresponding to blood flow using one or more of thermodilution measurements, impedance measurements, blood pressure measurements, and Doppler measurements.

4. The system of claim 2, wherein the external processor is programmed to automatically adjust one or both of heart rate of the heart and the expandable portion to induce tricuspid regurgitation in a controllable manner for the purposes of monitoring and optimizing hemodynamic parameters.

5. The system of claim 1, wherein the external processor is programmed to automatically adjust heart rate of the heart for the purposes of monitoring and optimizing hemodynamic parameters.

6. A catheter for monitoring or modifying hemodynamics of a heart of a patient, comprising:
an elongate member comprising a proximal end, a distal end, and a distal portion sized for introduction into a patient's body;
a regurgitation structure on the distal portion configured to be expanded radially away from the distal portion to open a tricuspid valve of the heart;
a blood pressure sensor; and
one or more electrodes on the distal portion to provide sensing and pacing of the heart.

7. A system for monitoring or modifying hemodynamics of a heart of a patient, comprising:
an elongate member comprising a proximal end, a distal end, and a distal portion sized for introduction into a patient's body;
an expandable regurgitation structure on the distal portion;
a pressure sensor for measuring pressure adjacent the regurgitation structure;
one or more electrodes on the distal portion; and
a controller coupled to the pressure sensor for acquiring pressure data to provide an indication when the regurgitation structure is positioned within a tricuspid valve of the heart, the controller coupled to the one or more electrodes to provide sensing and pacing the heart.

8. The system of claim 7, wherein the controller is configured for one or both of pacing the heart to increase heart rate and expanding the regurgitation structure to induce regurgitation.

9. The system of claim 8, the controller further configured to measure changes in performance of the heart to estimate one or both of volume responsiveness and optimal heart rates for the heart.

10. The system of claim 9, further comprising one or more sensors on the distal portion configured to provide sensor data corresponding to one of blood pressure and blood flow rate, and wherein the controller is coupled to the one or more sensors to analyze the sensor data from the one or more sensors to measure changes in performance of the heart.

11. The system of claim 10, wherein the one or more sensors are carried on a distal extension extending distally from the distal portion beyond the regurgitation structure sized for introduction into a pulmonary artery of the heart such that one or more sensors provide sensor data from the pulmonary artery.

12. The system of claim 11, wherein the one or more sensors comprise a blood pressure sensor for measuring pulmonary blood pressure within the pulmonary artery.

13. The system of claim 11, wherein the one or more sensors comprise a blood flow sensor for measuring blood flow through the pulmonary artery.

14. The system of claim 13, wherein the blood flow sensor comprises one of a Doppler sensor, an impedance sensor, and a temperature sensor.

15. The system of claim 7, wherein the controller is configured to:
one or both of:
pace the heart using the one or more electrodes to increase the heart rate of the patient; and
expand the regurgitation structure to cause tricuspid regurgitation; and
measure changes in performance of the heart based on one or both of the increased heart rate and the tricuspid regurgitation.

16. The system of claim 15, wherein the controller is further configured to modify one or more performance parameters of the heart based on the measured changes.

17. The system of claim 7, further comprising:
a distal extension extending distally from the distal portion of the elongate member beyond the regurgitation structure sized for introduction into a pulmonary artery of the heart;
a balloon on the distal extension; and
a distal sensor on the distal extension for providing data corresponding to one of blood pressure and blood flow rate within the pulmonary artery.

18. The system of claim 17, wherein the distal sensor comprises one of a pressure sensor, a Doppler sensor, an impedance sensor, and a temperature sensor.

19. The system of claim 7, further comprising an actuator on the proximal end of the elongate member and coupled to the regurgitation structure for selectively expanding and collapsing the regurgitation structure.

* * * * *